United States Patent
Nakamura

(10) Patent No.: US 7,152,475 B2
(45) Date of Patent: Dec. 26, 2006

(54) DEVICE AND METHOD FOR MEASURING AXIAL FORCE OF BOLT

(76) Inventor: Takanori Nakamura, 1-2, Konan 1-chome, Niigata-shi, Niigata 950-0855 (JP)

( * ) Notice: Subject to any disclaimer, the term of this patent is extended or adjusted under 35 U.S.C. 154(b) by 67 days.

(21) Appl. No.: 10/513,760

(22) PCT Filed: Jul. 9, 2003

(86) PCT No.: PCT/JP03/08707

§ 371 (c)(1),
(2), (4) Date: Nov. 9, 2004

(87) PCT Pub. No.: WO2004/011893

PCT Pub. Date: Feb. 5, 2004

(65) Prior Publication Data

US 2005/0223804 A1    Oct. 13, 2005

(30) Foreign Application Priority Data

Jul. 25, 2002    (JP) .............................. 2002-216773

(51) Int. Cl.
*G01N 3/34* (2006.01)
(52) U.S. Cl. .......................................... 73/581; 73/761
(58) Field of Classification Search ................. 73/581, 73/761, 579
See application file for complete search history.

(56) References Cited

U.S. PATENT DOCUMENTS 3,918,294 A * 11/1975 Makino et al. ............... 73/581
3,975,948 A * 8/1976 Makino et al. ............... 73/581
4,062,229 A * 12/1977 Godfrey et al. .............. 73/582
4,152,929 A    5/1979 Edmond et al.
4,318,302 A * 3/1982 Choi ........................... 73/761
5,024,090 A * 6/1991 Pettigrew et al. ............ 73/572

FOREIGN PATENT DOCUMENTS

| EP | 0087507 A | * | 9/1983 |
|---|---|---|---|
| GB | 2 370 120 | | 6/2002 |
| JP | 02264837 A | * | 10/1990 |
| JP | 5-26749 | | 2/1993 |
| JP | 11-148876 | * | 6/1999 |
| JP | 2998725 | | 11/1999 |
| JP | 2002-48660 | | 2/2002 |
| JP | 2002340710 A | * | 11/2002 |

* cited by examiner

*Primary Examiner*—Hezron Williams
*Assistant Examiner*—Nashmiya Fayyaz
(74) *Attorney, Agent, or Firm*—Manabu Kanesaka

(57) ABSTRACT

The present invention provides an axial bolt force measuring instrument for measuring an axial force of a bolt for a hub that couples a wheel and an axle of a vehicle, where the instrument is provided with a setting portion that sets a predetermined axial force of the bolt, a tapping portion that taps the bolt, a sound collecting portion that collects tap sound generated by tapping the bolt with the tapping portion, a frequency measuring portion that measures a frequency of the tap sound collected by the sound collecting portion, an axial force converting portion that converts the frequency of the tap sound measured by the frequency measuring portion into an axial force of the bolt, a comparing portion that compares the set axial force set in the setting portion with the converted axial force converted in the axial force converting portion from the frequency of the tap sound, and a display portion that displays a result of comparison in the comparing portion.

7 Claims, 4 Drawing Sheets

DEVICE AND METHOD FOR MEASURING AXIAL FORCE OF BOLT

TECHNICAL FIELD

The present invention relates to an axial bolt force measuring instrument and method for measuring an axial force (tightening force) of a bolt, and more particularly, to an axial bolt force measuring instrument for measuring an axial force (tightening force) of a bolt for a hub that couples a wheel and an axle of a vehicle i.e. a hub bolt that fastens the wheel to the hub.

BACKGROUND ART

Generally, a wheel of a vehicle is coupled to an axle through a hub. In this case, the wheel and hub are fastened by a bolt (hereinafter referred to as a hub bolt) and nut. When the nut is fixed and the hub bolt is rotated in the fastening direction, the wheel and hub are compressed, while a tension (axial force or tightening force) is applied to the hub bolt, and the hub bolt extends. In the assembling operation or the like, it is important to adequately control the tightening fore (axial force) of the hub bolt to maintain at a proper value. This is because of a risk that the hub and/or wheel is deformed or broken, when the fastening is not adequate and/or tightening is excessively applied.

Various methods have conventionally been known, as a method for controlling the tightening force (axial force) of a hub bolt. For example, methods have been well known that a tightening torque is set at a predetermined value using a torque wrench, or a skilled mechanic or the like taps each portion of a bolt fastening member using a micro hammer, and based on the tap sound, inspects a tightening state of the hub bolt. Further, an ultrasonic applying measurement tester has also been known which applies ultrasonic pulses to a tightened hub bolt from an end surface in the axial direction, obtains a length (elongation) of the hub bolt from the time required for the reflective wave to return, and using the bolt length, calculates the axial force of the hub bolt.

However, in the method of using the torque wrench, the use is predicated on the muscular strength of a person, and therefore, limited to small-size vehicles or the like. In this torque wrench method, since the tightening torque is set at a predetermined value and the bolt is merely tightened to the set value, it is not possible to examine and/or measure the axial force itself of the hub bolt after the bolt is tightened. Further, in the torque wrench method, an unstable factor of torque coefficients is considered as a defect.

Meanwhile, in the inspection method using the tap sound with a micro hammer, since decision is made by listening based on the skill and intuition without the rating, it is not possible to examine and/or measure a fastening state of the hub bolt with accuracy.

Further, in the method using the ultrasonic applying measurement tester, since the axial force of the hub bolt is obtained by calculating an elongation of the hub bolt targeted for the test using correlation, it is required to perform measurement at least twice, prior to and subsequent to bolt fastening, to determine the elongation of the hub bolt. Accordingly, there are limitations in time required for measurement and reduction in cost. Furthermore, the conventional ultrasonic applying measurement tester has a separate sensor portion and amplifier portion and thus a plurality of components, thereby is not suitable for operation requiring portability, nor does not have a power source, and therefore, can be used only in places with a commercial power source.

DISCLOSURE OF INVENTION

It is an object of the present invention to provide an axial bolt force measuring instrument with excellent portability and general versatility enabling the axial force (fastening state) of a tightened bolt to be measured promptly and accurately.

Therefore, the present invention provides an axial bolt force measuring instrument which measures an axial force of a bolt for a hub that couples a wheel and an axle of a vehicle, and which is integrally provided with a setting portion that sets a predetermined axial force of the bolt, an initiation operation portion that is operated to start measurement, a tapping portion which is brought into contact with the bolt, and is operated by initiation operation from the initiation operation portion to tap the bolt continuously a plurality of times in a predetermined stroke, a sound collecting portion which is brought into contact with the bolt and collects tap sound generated by the tapping portion tapping the bolt, a frequency measuring portion that measures a frequency of the tap sound collected by the sound collecting portion, an axial force converting portion that converts the frequency of the tap sound measured by the frequency measuring portion into an axial force of the bolt, a comparing portion that compares a set axial force set in the setting portion with a converted axial force converted in the axial force converting portion from the frequency of the tap sound, and a display portion that displays a result of comparison in the comparing portion.

BEST MODE FOR CARRYING OUT THE INVENTION

A preferred embodiment of the present invention will specifically be described below with reference to accompanying drawings.

Figure 1:
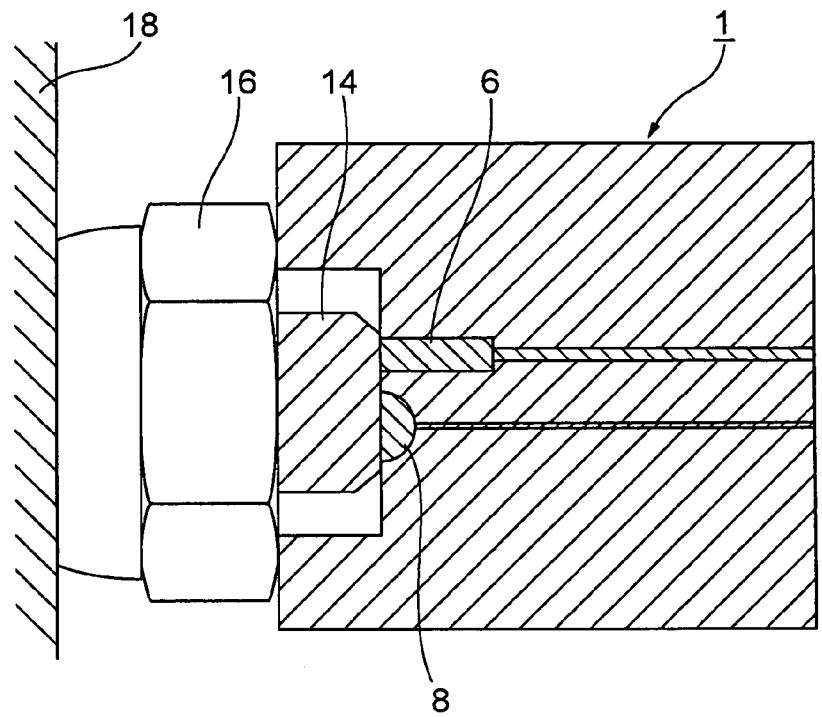
FIG. 1 is a conceptual view of a primary portion enlarged section of an axial bolt force measuring instrument according to the present invention.
Figure 2:
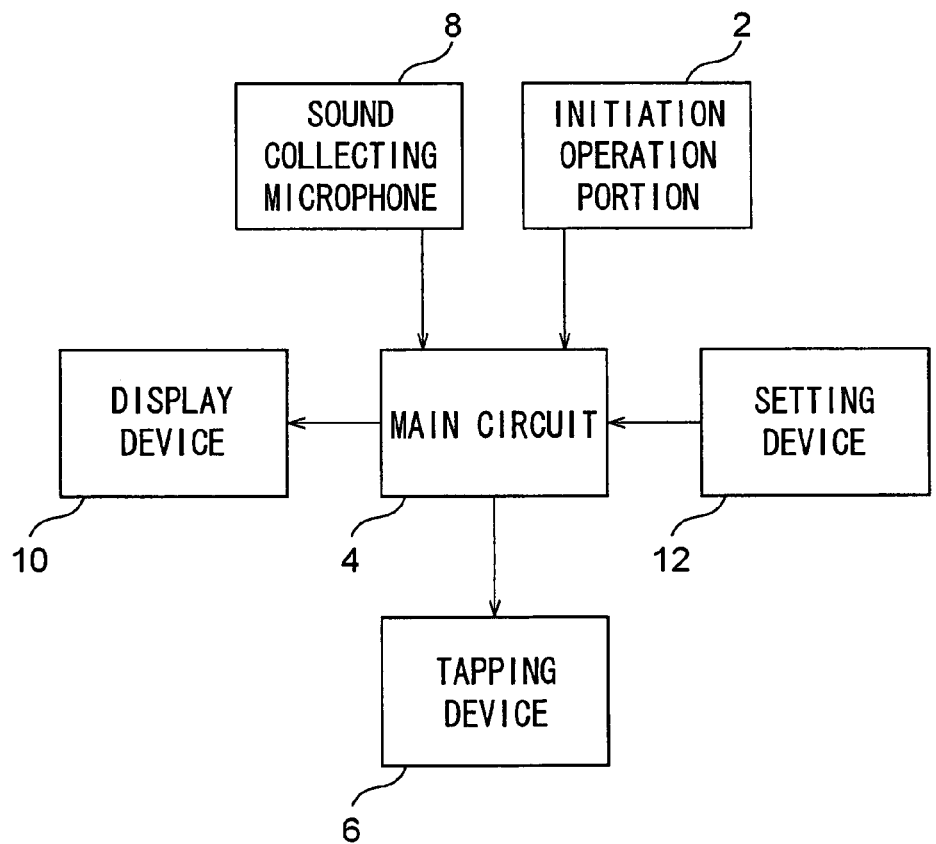
FIG. 2 is a schematic block diagram of the axial bolt force measuring instrument according to the present invention.

FIGS. 1 and 2 conceptually show an axial bolt force measuring instrument according to the present invention. As can be seen from the figures, the axial bolt force measuring instrument according to the present invention taps a hub bolt, and measures an axial force of the bolt from the frequency of the tap sound. First, the principle will be described below.

Generally, when a tension is generated on an object and the object is hit, unique sound is generated. The frequency of the hit sound varies with level of the tension of the hit object (representative examples of application of this principle are musical instruments, and tuning of a piano, guitar or the like is performed by increasing/decreasing the tension of chords). For example, when a rigid body under a tension is hit by an object with a higher degree of hardness than that of the rigid body, the frequency of the hit sound caused by hitting has the correlation with the tension of the rigid body, and increases as the tension is higher, while decreasing as the tension is lower. In practical phenomenon, for example, the sound with a high frequency occurs generally in a normal fastening portion (when normal tension occurs on a rigid body) in a metal component subjected to heat processing, while the dull sound with a low frequency occurs in portions with corrosion, breakage, distortion, crack, etc.

It is a basic concept of the present invention to apply the aforementioned principle to measurement of an axial bolt force. In other words, fastening a bolt and nut is the operation for generating a tension on the bolt, and whether or not the bolt is tightened by a predetermined tightening torque (axial force) can be determined by measuring whether or not a predetermined tension is generated on the bolt. Further, the tension is measured from the frequency of the hit sound by hitting the bolt.

Based on such a principal, as shown in FIGS. 1 and 2, an axial bolt force measuring instrument 1 according to the present invention is provided with an initiation operation portion 2 to be operated to start measurement, a main circuit 4 that receives an initiation signal from the initiation operation portion 2, a tapping device 6 which is brought into contact with a bolt 14 subject to measurement and based on a control signal from the main circuit 4 due to the initiation signal, operates and hits the bolt 14, a sound collecting microphone 8 that collects hit sound (tap sound) from the bolt 14 by the tapping device 6, a setting device 12 to set and input a proper axial force (predetermined value) of the bolt subject to measurement, for example, at a predetermined range, and a display device 10 that displays a result of measurement.

In this configuration, the frequency of the hit sound collected by the sound collecting microphone 8 is measured, and the measured value is compared with a reference value in the main circuit 4. More specifically, the main circuit 4 has a storage portion that stores correlation data (that is beforehand determined by experiments or the like) between the frequency and the axial bolt force (tension), obtains an axial bolt force corresponding to the frequency measured value from the correlation data stored in the storage portion, and determines whether or not the axial bolt force agrees with a proper value (reference value) set and input by the setting device 12 (whether or not the axial bolt force converted from the frequency is in a range of proper values set and input by the setting device 12, when a predetermined range is set and input as the proper axial force) by comparison. Then, the result of determination is displayed on the display device 10. In addition, in FIG. 1, "16" denotes a nut combined with the bolt 14, and "18" denotes a member fastened by the bolt 14 and nut 16.

As described above, the axial bolt force measuring instrument 1 according to the present invention causes the tapping device 6 to hit the bolt 14, measures the frequency of the hit sound generated by hitting, compares the measured value with a reference value (a single value (or a range of values) set and input by the setting device), and thus functions as a tester that inspects and diagnoses the level of the axial force (tension) of the bolt 14. As is understood from the foregoing, the basic use mode of the axial bolt force measuring instrument according to the present invention is similar to that of the previously-mentioned conventional method for lightly hitting each portion of the construction using a micro hammer to inspect. However, the method using the axial bolt force measuring instrument according to the present invention is to accurately measure the axial force of the bolt by detecting the tap sound electrically to process, and in this respect, has the most significant difference from the conventional inspection method using a micro hammer which makes a decision by listening based on the skill and intuition without the rating.

An embodiment of the present invention based on the aforementioned principal will be described specifically below with reference to FIGS. 3 to 6.

Figure 3:
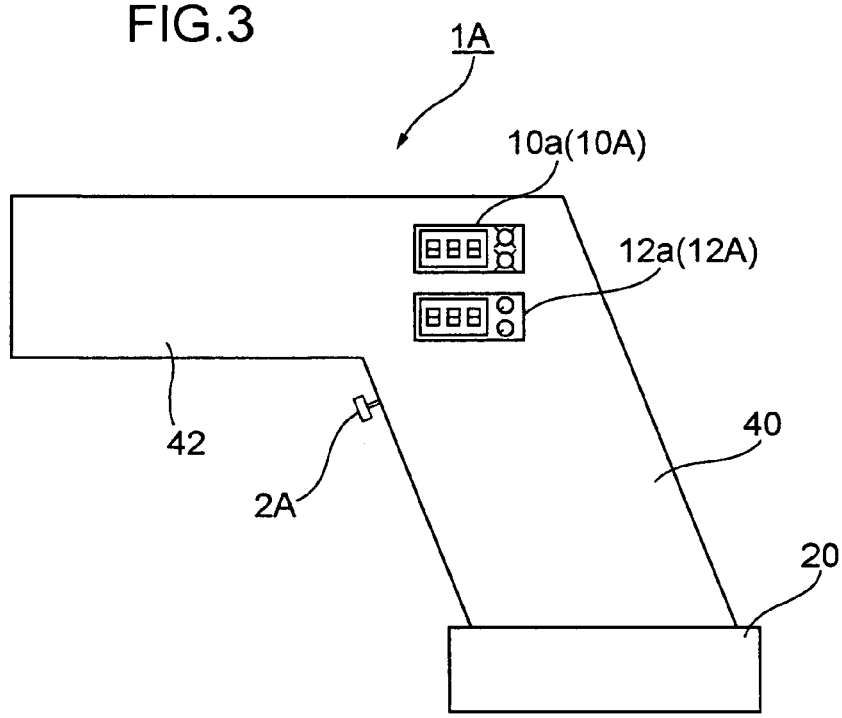
FIG. 3 is a side view of an axial bolt force measuring instrument according to one embodiment of the present invention.
Figure 4:
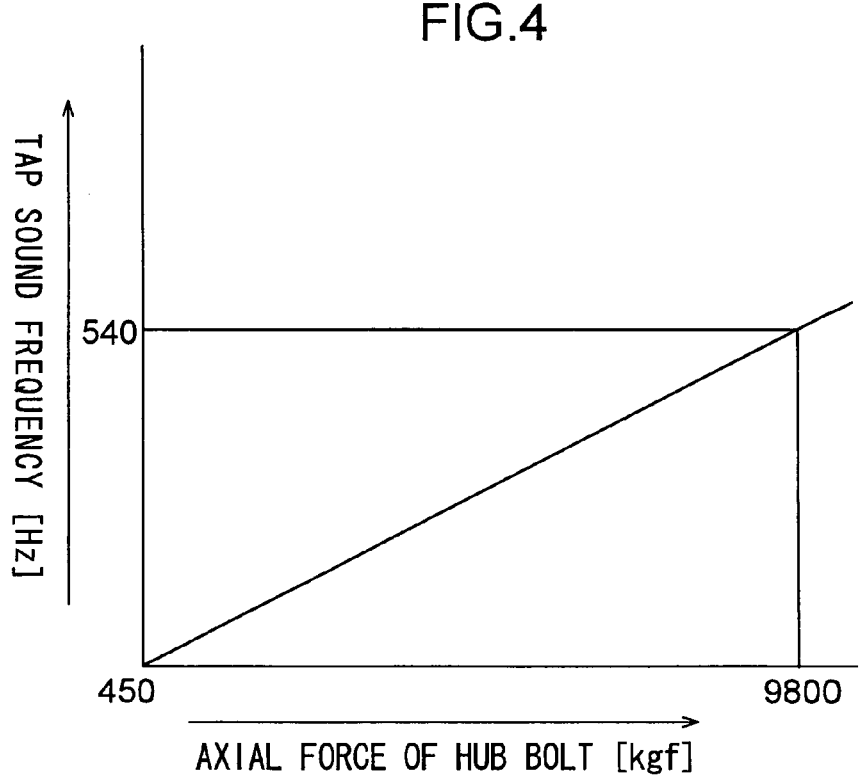
FIG. 4 is a graph showing the correlation between the axial bolt force and the frequency of tap sound.
Figure 5:
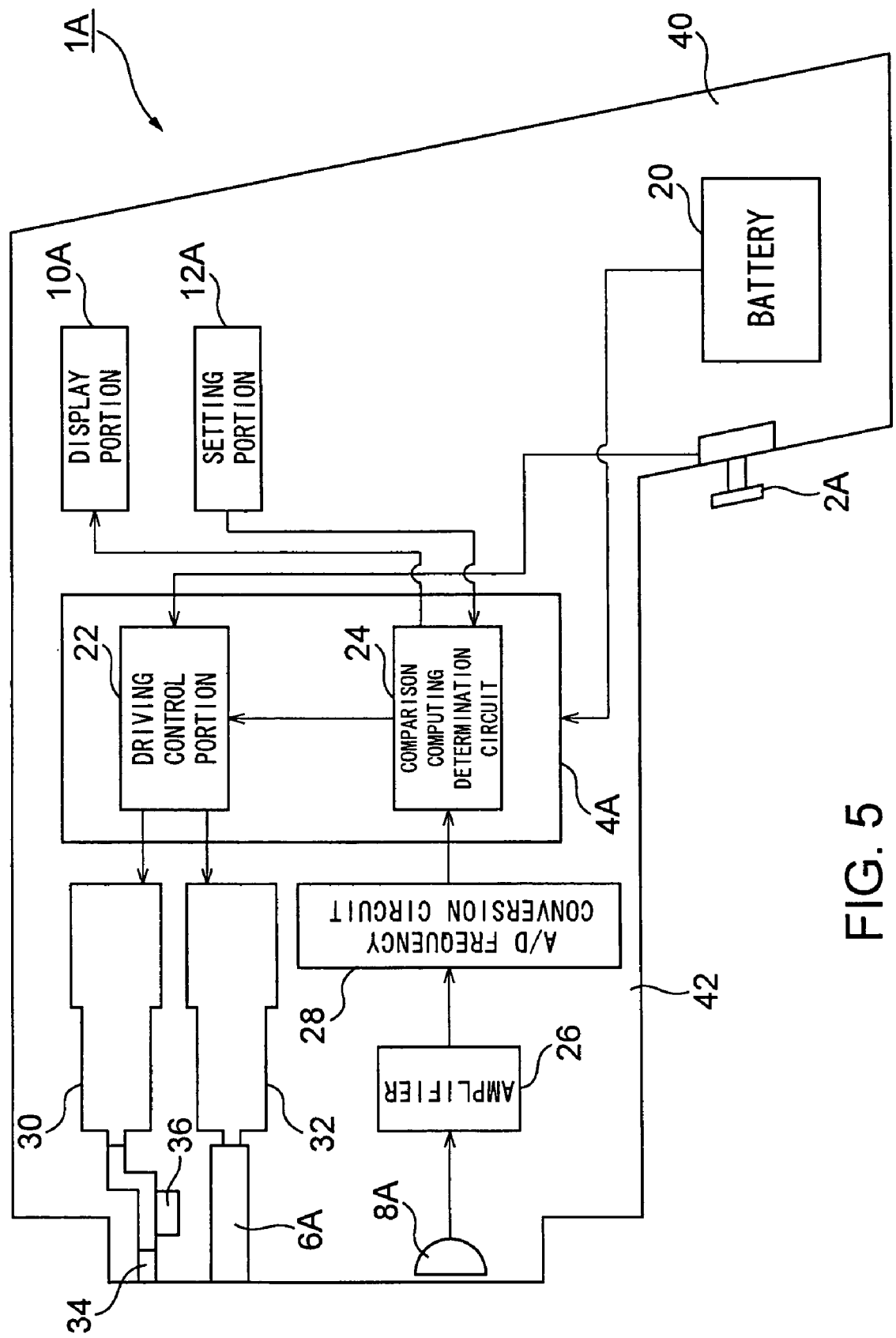
FIG. 5 is a schematic internal configuration view of the axial bolt force measuring instrument according to one embodiment of the present invention.

As shown in FIGS. 3 to 5, an axial bolt force measuring instrument 1A of this embodiment has a substantially gun-shaped form, and comprised of a gun-barrel-shaped main body portion (measuring instrument body) 42 and a handle portion 40 enabling grasp thereof by hand. The handle portion 40 is provided with a trigger lever 2A as an initiation operation portion capable of being operated by a finger of the hand grasping the handle portion 40 to start measurement. The trigger lever 2A is electrically connected to a driving control portion 22 of a main substrate (main circuit) 4A described later. Further, inside the handle portion 40 is provided a battery 20 that supplies power to each electrical component (described later) including the main substrate 4A.

The main body portion 42 is provided with a setting portion 12A in which, for example, a predetermined range is set and input as a proper axial force (reference value; predetermined value) of the bolt subject to measurement, and a display portion 10A that displays a result of measurement. The display portion 10A has a display panel 10a exposed on the side wall of the main body portion 42 as shown in FIG. 3. The display panel 10a is provided with a plurality of LEDs (display means) capable of displaying a result of measurement (determination) of whether or not the measured axial force of the bolt is a proper axial force, for example, in a plurality of modes, and a display that displays a measured value of the axial bolt force. Meanwhile, the setting portion 12A also has a setting panel 12a exposed on the side wall of the main body portion 42 as shown in FIG. 3. The setting panel 12a is provided with at least various kinds of setting buttons to set the size of the bolt to measure and others pertinent to the correlation data described later, and a display that displays values set by the setting buttons. In addition, the display portion 10A and setting portion 12A are electrically connected to a comparison computing determination circuit 24, described later, of the main substrate 4A.

On the front end surface of the main body portion 42 is provided an impact chip 6A as a tapping device (tapping portion) that comes into contact with the bolt subject to measurement and that continuously hits the bolt. The hardness of the impact chip 6A is set higher than the hardness of the bolt subject to measurement.

The impact chip 6A is attached to the tip of a plunger solenoid 32 that is electrically connected to the driving control portion 22 of the main substrate 4A, and continuously hits the bolt by a traveling driving portion of the plunger solenoid 32 traveling back and forth in a stroke of about 5 mm using a control signal from the driving control portion 22 (for example, the chip 6A operates for about two seconds at speed of tapping three times a second).

Further, on the front end surface of the main body portion 42 is provided a sound collecting microphone (sound collecting portion) 8A that collects hit sound (tap sound) generated by tapping the bolt by the impact chip 6A. The sound collecting microphone 8A is electrically connected to the comparison computing determination circuit 24 of the main substrate 4A via an amplifier 26 and an A/D frequency conversion circuit (frequency measuring portion) 28. In this case, the amplifier 26 amplifies a sound signal due to the hit sound collected by the sound collecting microphone 8A. The A/D frequency conversion circuit 28 converts the sound signal as an analog signal amplified by the amplifier 26 into a digital signal to output to comparison computing determination circuit 24.

Furthermore, on the front end surface of the main body portion 42 is provided an inkjet nozzle 34 capable of providing the bolt with marking, for example, of a result of measurement. The inkjet nozzle 36 is connected to a plunger solenoid valve 30 that is electrically connected to the driving control portion 22 of the main substrate 4A, and sprays ink from an ink tank 36 to the bolt by the operation of the plunger solenoid valve 30.

The main substrate 4A is provided with the driving control portion 22 and the comparison computing determination circuit (comparing portion; axial force converting portion) 24. The driving control portion 22 generates a control signal to drive the plunger solenoid 32 of the impact chip 6A in response to a trigger signal due to the operation of the trigger lever 2A, and further generates a control signal to drive the plunger solenoid valve 30 of the ink jet nozzle 34 in response to a determination signal from the comparison computing determination circuit 24.

Meanwhile, the comparison computing determination circuit 24 receives a digital signal with the frequency corresponding to the hit sound collected by the sound collecting microphone 8A from the A/D frequency conversion circuit 28, converts (computes) the frequency data of the digital signal into an axial bolt force, while comparing the converted value with a set value (predetermined proper axial bolt force) set and input in the setting portion 12A, and determines whether or not the axial bolt force is proper.

More specifically, the comparison computing determination circuit 24 stores the correlation data (that is beforehand obtained from experiments or the like) between the tap sound frequency (the frequency of hit sound by tapping the bolt by the impact chip 6A) and the axial bolt force, obtains an axial bolt force corresponding to the measured frequency value (of the digital signal received from the A/D frequency conversion circuit 28) from the stored correlation data, and determines whether or not the axial bolt force agrees with the set value set and input in the setting portion 12A (whether or not the axial bolt force converted from the frequency measured value is in a range of the proper value set and input in the setting portion 12A, when a predetermined range is set and input as the proper axial force) by comparing the values. The correlation data between the frequency and axial bolt force is stored for each size of the bolt and for each material of the bolt and a member related to bolt fastening. When the size, material and others of the bolt to measure are set in the setting portion 12A, the comparison computing determination circuit 24 converts the frequency measured value into the axial bolt force using the correlation data corresponding to the set value.

In addition, a parameter other than the size of the bolt and materials may be adopted for the correlation data. As an example of the correlation data, FIG. 4 shows the correlation data between the tap sound frequency and the axial bolt force of an M20 bolt (surface hardness 454 HV) with a strength class of 12.9 that is a central class of 1.8T series in JIS B1051 Table 1–7.

With reference to a flowchart in FIG. 6, a case will be described below of measuring an axial force of a bolt for a hub that couples a wheel and an axle of a vehicle i.e. a hub bolt to fasten the wheel to the hub.

In addition, in this case, the hub corresponds to the member 18 in FIG. 1, the hub nut corresponds to the nut 16 in FIG. 1, and the hub bolt corresponds to the bolt 14 in FIG. 1. In the case of measuring the axial bolt force of a middle-size vehicle using hub bolts with a nominal bolt diameter of 18 mm to 20 mm (M18~M22), for example, when the surface hardness of the hub bolt with the nominal diameter of 20 mm (M20) is 454 HV in JIS, the surface hardness of the impact chip 6A is set at 520 HV harder than 454 HV. Further, it is assumed that the comparison computing determination circuit 24 stores the correlation data between the tap sound frequency and the axial bolt force in a no-load state where any load is not mounted on the vehicle for each size of the hub bolt and for each material of the hub bolt and of the wheel.

Figure 6:
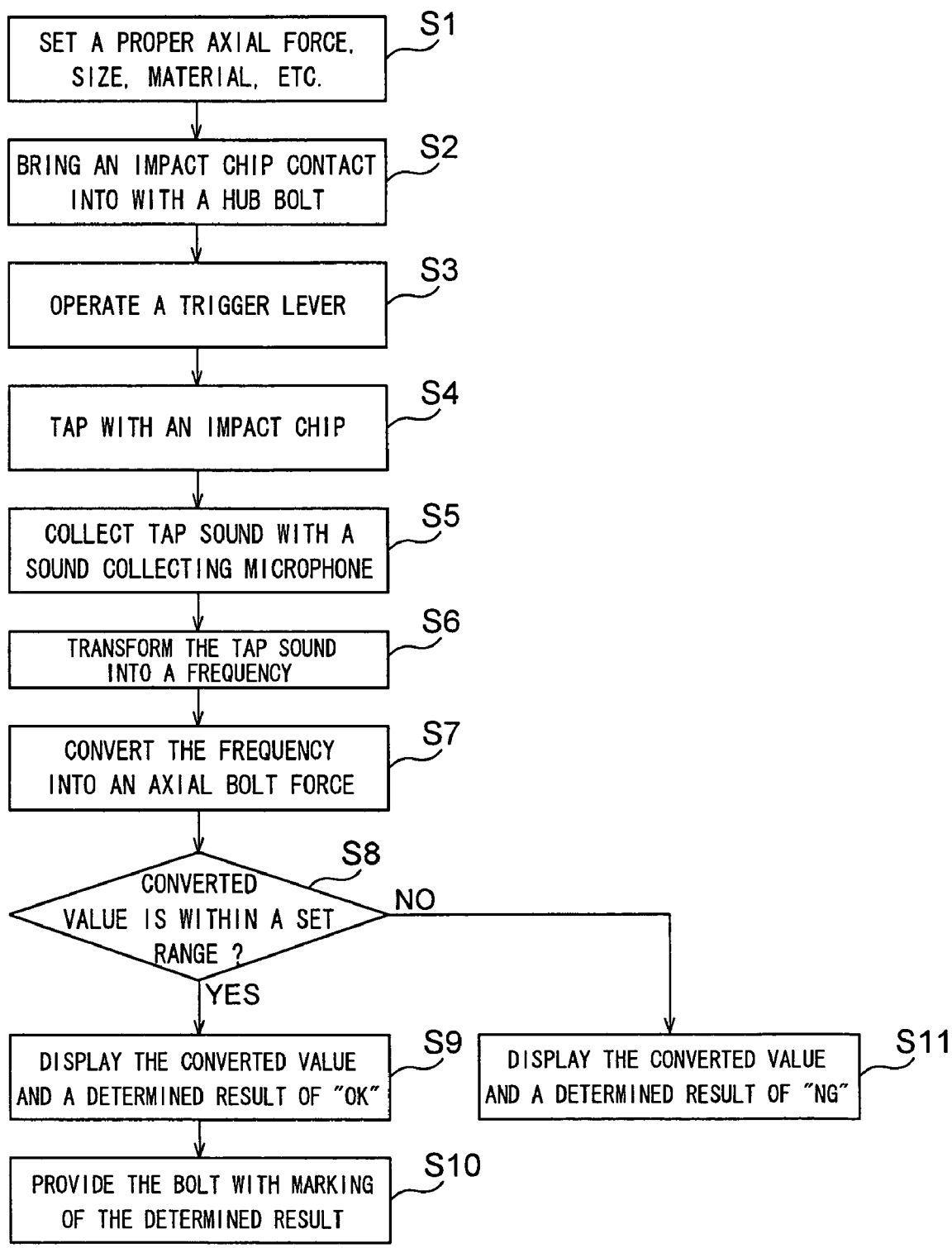
FIG. 6 is a flowchart showing measuring procedures of the axial bolt force measuring instrument according to one embodiment of the present invention.

First, operating the setting buttons in setting portion 12A, a proper axial force (rating value) of a hub bolt subject to measurement is set, for example, at a predetermined range (a single value is also available), and the size of the hub bolt, materials and others are set (step S1 in FIG. 6). For example, it is assumed that M20 is set as the bolt size, and that the material of the hub bolt and the material (aluminum or steel) of the wheel to be fastened by the hub bolt are set as the materials. By this means, the comparison computing determination circuit 24 performs comparison and determination using the correlation data between the tap sound frequency and the axial bolt force corresponding to set parameters. Further, as a proper axial force, for example, a range of 7,500 kgf to 15,000 kgf (or a single value of 9,800 kfg that is a standard axial force) is set.

Then, in a no-load state where any load is not mounted on the vehicle (because the correlation data of the no-load state is stored in comparison computing determination circuit 24 herein), the impact chip 6A on the front end surface of the axial bolt force measuring instrument 1A is brought into contact with the end surface of the hub bolt (step S2 . . . the state in FIG. 1).

When the impact chip 6A comes into contact with the end surface of the bolt, the trigger lever 2A is depressed to operate (step S3). In this way, a trigger signal is input to the driving control portion 22 from the trigger lever 2A side, and in response to the signal, the driving control portion 22 outputs a control signal to drive the plunger solenoid 32 to the plunger solenoid 32. As a result, the traveling driving portion of the plunger solenoid 32 travels back and forth in a stroke of about 5 mm, and continuously hits the end surface of the hub bolt (step S4). Herein, for example, the portion hits for about two seconds at speed of about 3 taps/second.

The tap sound generated by hitting is collected by the sound collecting microphone 8A (step S5), while being amplified by the amplifier 26. Then, the sound signal as an amplified analog signal is transformed into a frequency (step S6), and output to the comparison computing determination circuit 24 as a digital signal.

When the frequency data of the tap sound collected by the sound collecting microphone 8A is thus input to the comparison computing determination circuit 24, comparison computing determination circuit 24 converts the input frequency data into an axial bolt force (step S7) using the correlation data of tap sound frequency/axial bolt force corresponding to the size of the hub bolt and materials of the hub bolt and the wheel set in the setting portion 12A, and determines whether or not the converted value agrees with the set value set and input in the setting portion 12A

(whether or not the converted value is in a range of proper values set and input in the setting portion 12A, when a predetermined range is set and input as the proper axial force) by comparing the values (step S8). Then, when determining that the converted value agrees with the set value (or is in the set range), the comparison computing determination circuit 24 displays the converted value (measured axial bolt force) on the display of the display potion 10A, while lighting the LED, for example, displaying "OK" of the display portion 10A (step S9). Further, at the same time, the comparison computing determination circuit 24 outputs a signal indicating that the measured axial bolt force is proper to the driving control portion 22. By this means, the plunger solenoid valve 30 is driven by the driving control portion 22, the ink is sprayed to the bolt from the ink tank 36 via the inkjet nozzle 34, and the bolt is thus provided with marking indicating such a result of determination that the axial bolt force is proper (step S10).

Meanwhile, when determining that the converted value does not agree with the set value (or is not in the set range), the comparison computing determination circuit 24 displays the converted value (measured axial bolt force) on the display of the display potion 10A, while lighting the LED, for example, displaying "NG" of the display portion 10A (step S11). At this point, for example, the LED displaying "HI" or "LOW" may be lighted, in order to specifically display whether the converted value exceeds or falls below the set value.

As described above, the axial bolt force measuring instrument according to the present invention uses that the correlation exists between the tap sound frequency of a bolt and the axial force of the bolt, and is provided with the tapping portion (6 and 6A) that taps the bolt, the sound collecting portion (8 and 8A) that collects tap sound generated by tapping the bolt with the tapping portion (6 and 6A), the frequency measuring portion (28) that measures the frequency of the tap sound collected by the sound collecting portion (28), and the axial force converting portion (24) that converts the frequency of the tap sound measured by the frequency measuring portion (28) into an axial force of the bolt. Accordingly, without having the skill, intuition and/or specific knowledge and experiment, it is possible to accurately measure the axial bolt force (fastening state subsequent to fastening of the bolt) with ease in a short time, and targets for measurement are not limited particularly (excellent in general versatility) because of not depending on the muscular strength of a person.

Further, the axial bolt force measuring instrument according to one embodiment of the present invention is provided with the setting portion (12 and 12A) to set a predetermine axial bolt force, and the comparing portion (24) that compares the set axial force set in the setting portion (12 and 12A) with a converted axial force converted in the axial force converting portion (24) from the tap sound frequency. Therefore, it is possible to accurately recognize whether or not the bolt subject to measurement has a predetermined axial force (whether the bolt is tightened by a predetermined tightening force), i.e. lack of tightening, forgetting to tighten or excess tightening of the bolt.

Furthermore, in the axial bolt force measuring instrument according to one embodiment of the present invention, the axial force converting portion (24) converts the tap sound frequency into an axial bolt force corresponding to various parameters such as the size of the bolt and materials of the bolt and member to fasten by the bolt. Therefore, it is possible to perform accurate frequency-axial force conversion, and thus the accuracy is improved in measuring the axial bolt force.

Still furthermore, the axial bolt force measuring instrument according to one embodiment of the present invention is formed of the measuring instrument body (42) internally provided with the tapping portion (6 and 6A), sound collecting portion (8 and 8A), frequency measuring portion (28), and axial force converting portion (24), and of the handle portion (40) which enables grasp thereof by hand, extends from the measuring instrument body (42) and has the initiation portion (2 and 2A) to initiate the tapping portion (6 and 6A), and has the internal battery (20) that supplies power required for measurement of the axial bolt force. It is thus possible to use the instrument at any places readily (with excellence in portability) without restrictions in indoor and outdoor weather conditions and power supply.

In addition, as a matter of course, the present invention is not limited to the aforementioned embodiment, and is capable of being carried into practice with various modifications thereof without departing from the subject matter of the present invention. For example, the display portion 10A displays a measured value as an axial bolt force (kgf) in the aforementioned embodiment, but may display a tightening torque (T), tension (N), or tap sound frequency (Hz) as a measured value. Further, the setting portion 12A enables setting and input of a predetermined axial bolt force, but may enable setting and input of a tap sound frequency corresponding to the predetermined axial bolt force. In this case, without using the correlation data to convert the tap sound frequency into the axial bolt force, it is possible to directly compare a measured frequency with the set frequency in the comparison computing determination circuit 24. This scheme is effective in the case where the tap sound frequency is beforehand obtained corresponding to the proper axial force. Further, in this case, by causing the display portion 10A to display a measured tap sound frequency, instead of a measured axial force, the measuring instrument becomes a bolt tap sound frequency measuring instrument, rather than the axial bolt force measuring instrument. Furthermore, in the aforementioned embodiment, the setting portion 12A is provided so as to response to axial force measurements with various bolt sizes and materials, and corresponding to parameters set and input in the setting portion 12A, the correlation data is selected and an axial force is measured from the tap sound frequency. However, in the case where the axial bolt force measuring instrument is used only for bolts with a predetermined size and material, since the common correlation data is used, the need is eliminated of providing the setting portion on purpose.

The invention claimed is:

1. An axial bolt force measuring instrument for measuring an axial force of a bolt for a hub that couples a wheel and an axle of a vehicle, the instrument comprising:
   a setting portion that sets a predetermined axial force of the bolt;
   an initiation operation portion that is operated to start measurement;
   a tapping portion against which the bolt abuts, the tapping portion further comprising an impact chip that comes in contact with the bolt, the tapping portion being operated by an initiation operation of the initiation operation portion to continuously tap the bolt a plurality of times with a predetermined stroke;
   a sound collecting portion which is brought into contact with the bolt, and collects tap sound generated by the tapping portion tapping the bolt;

a frequency measuring portion that measures a frequency of the tap sound collected by the sound collecting portion;

an axial force converting portion that converts the frequency of the tap sound measured by the frequency measuring portion into an axial force of the bolt;

a comparing portion that compares a set axial force set in the setting portion with a converted axial force converted in the axial force converting portion from the frequency of the tap sound; and a display portion that displays a result of a comparison performed by the comparing portion, wherein the instrument is a one-piece instrument.

2. The axial bolt force measuring instrument according to claim 1, wherein the impact chip comprises a hardness greater than a hardness of the bolt subject to measurement.

3. The axial bolt force measuring instrument according to claim 1, wherein the display portion displays the axial force of the bolt converted in the axial force converting portion.

4. The axial bolt force measuring instrument according to claim 1, wherein the axial force converting portion converts the frequency of the tap sound into the axial force of the bolt corresponding to a size of the bolt.

5. The axial bolt force measuring instrument according to claim 4, wherein the axial force converting portion converts the frequency of the tap sound into the axial force of the bolt corresponding to a material of the bolt and a material of a member fastened by the bolt.

6. The axial bolt force measuring instrument according to claim 1, wherein the instrument is formed of:

an instrument body internally provided with the tapping portion, the sound collecting portion, the frequency measuring portion, and the axial force converting portion; and a handle portion which enables grasp thereof by hand, extends from the instrument body, and has an initiation portion that initiates the tapping portion.

7. The axial bolt force measuring instrument according to claim 6, further comprising:

an internal battery that supplies power required for measurement of the axial force of the bolt.

* * * * *